United States Patent
Zahos

(10) Patent No.: US 8,088,084 B2
(45) Date of Patent: Jan. 3, 2012

(54) METHOD AND APPARATUS FOR REPAIR OF INTERVERTEBRAL DISCS

(75) Inventor: Peter A. Zahos, Weston, FL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 761 days.

(21) Appl. No.: 12/043,471

(22) Filed: Mar. 6, 2008

(65) Prior Publication Data

US 2008/0221490 A1 Sep. 11, 2008

Related U.S. Application Data

(60) Provisional application No. 60/905,210, filed on Mar. 6, 2007.

(51) Int. Cl.
*A61H 1/00* (2006.01)
*A61B 8/00* (2006.01)
(52) U.S. Cl. .............. 601/2; 600/437; 600/438
(58) Field of Classification Search .......... 600/439, 600/549, 438, 639, 437; 601/2, 3; 607/89, 607/116, 117, 99; 606/15, 16, 3, 180, 167
See application file for complete search history.

(56) References Cited

U.S. PATENT DOCUMENTS

| | | | |
|---|---|---|---|
| 4,530,360 A | | 7/1985 | Duarte |
| 5,762,616 A | | 6/1998 | Talish |
| 5,948,008 A | * | 9/1999 | Daikuzono ............... 607/89 |
| 5,971,949 A | | 10/1999 | Levin et al. |
| 5,997,490 A | | 12/1999 | McLeod et al. |
| 6,007,570 A | | 12/1999 | Sharkey et al. |
| 6,190,336 B1 | * | 2/2001 | Duarte et al. ............... 601/2 |
| 6,254,553 B1 | * | 7/2001 | Lidgren et al. ............. 601/3 |
| 6,355,006 B1 | | 3/2002 | Ryaby et al. |
| 6,368,292 B1 | * | 4/2002 | Ogden et al. .............. 601/2 |
| 6,562,033 B2 | | 5/2003 | Shah et al. |
| 6,582,392 B1 | | 6/2003 | Bennett et al. |
| 6,673,063 B2 | | 1/2004 | Brett |
| 6,726,685 B2 | | 4/2004 | To et al. |
| 6,736,835 B2 | | 5/2004 | Pellegrino et al. |
| 6,997,941 B2 | | 2/2006 | Sharkey et al. |
| 2002/0151940 A1 | * | 10/2002 | Bar-Cohen et al. ........ 607/99 |
| 2003/0069569 A1 | | 4/2003 | Burdette et al. |

(Continued)

FOREIGN PATENT DOCUMENTS

WO WO-99/19025 A1 4/1999

(Continued)

OTHER PUBLICATIONS

Glazer et al., "Use of Ultrasound in Spinal Arthrodesis", *Spine* 1998;23:1142-1148.

(Continued)

*Primary Examiner* — Long V. Le
*Assistant Examiner* — Lawrence Laryea
(74) *Attorney, Agent, or Firm* — Tarolli, Sundheim, Covell & Tummino LLP

(57) ABSTRACT

A method of repairing an intervertebral disc of a patient's body includes identifying a target area of the intervertebral disc. An ultrasound generator is placed proximate the target area and outside the patient's body. An area temperature at the target area is monitored. Ultrasonic energy is generated with the ultrasound generator within a predetermined energy range. The ultrasonic energy is adjusted in response to the area temperature exceeding a predetermined temperature range. An apparatus for repairing an intervertebral disc of a patient's body is also provided.

12 Claims, 4 Drawing Sheets

U.S. PATENT DOCUMENTS

| | | | |
|---|---|---|---|
| 2003/0153849 A1* | 8/2003 | Huckle et al. | 601/2 |
| 2003/0163066 A1* | 8/2003 | Lidgren | 601/2 |
| 2003/0216721 A1 | 11/2003 | Diederich et al. | |
| 2003/0225331 A1* | 12/2003 | Diederich et al. | 600/437 |
| 2006/0224223 A1* | 10/2006 | Podhajsky et al. | 607/117 |
| 2006/0241576 A1 | 10/2006 | Diederich et al. | |
| 2007/0239080 A1* | 10/2007 | Schaden et al. | 601/4 |

FOREIGN PATENT DOCUMENTS

| | | |
|---|---|---|
| WO | WO-99/48621 A2 | 9/1999 |

OTHER PUBLICATIONS

Emami et al., "No Effect of Low-Intensity Ultrasound on Healing Time of Intramedullary Fixed Tibial Fractures", *Journal of Orthopaedic Trauma* 1999;13:252-257.

Cook et al., "Low-Intensity Pulsed Ultrasound Improves Spinal Fusion", *The Spine Journal* 2001;1:246-254.

Brehm et al., "Stem Cells—Clinical Application and Perspectives", *Herz* 2002;27:611-620.

Crisci et al., "Low-Intensity Pulsed Ultrasound Accelerates the Regeneration of the Sciatic Nerve After Neurotomy in Rats", *Ultrasound in Med. & Biol.* 2002;28:1335-1341.

Duda et al., "Does Low-Intensity Pulsed Ultrasound Stimulate Maturation of Tissue-Enginerred Cartilage?", *Wiley Periodicals, Inc., J. Biomed. Mater. Res. Part B:Appl. Biomaier* 2004;68B:21-28. Abstract Only.

Frangioni et al., "In Vivo Tracking of Stem Cells for Clinical Trials in Cardiovascular Disease", *Circulation* 2004;110:3378-3384.

Haake et al., "Manipulation of Cells Using an Ultrasonic Pressure Field", *Ultrasound in Med. & Biol.* 2005;31:857-864.

Kim et al., "High-Throughput Cell Manipulation Using Ultrasound Fields", from Proceddings of the 26th Annual International Conference of the IEEE/EMBS, Sep. 1-5, 2004, 2571-2574.

van Wamel et al., "Micromanipulation of Endothelial Cells: Ultrasound-Microbubble-Cell Interaction", *Ultrasound in Med. & Biol.*2004;30:1255-1258.

Iwabuchi et al., "In Vitro Evaluation of Low-Intensity Pulsed Ultrasound in Herniated Disc Resorption", *Biomaterials* 2005;26:7104-7114.

Miyamoto et al., "Exposure to Pulsed Low Intensity Ultrasound Stimulates Extracellular Matrix Metabolism of Bovine Intervertebral Disc Cells Cultured in Alginate Beads", *Spine* 2005:30:2398-2405.

Nau et al., "Feasibility of Using Interstitial Ultrasound for Intradiscal Thermal Therapy: A Study in Human Cadaver Lumbar Discs", *Phys. Med. Biol.* 2005;50:2807-2821.

Cui et al., "Effects of Low-Intesnity Ultrasound on Chondrogenic Differentiation of Mesenchymal Stem Cells Embedded in Polyglycolic Acid: An in Vivo Study", *Tissue Engineering* 2006:12. Abstract Only.

Iwashina et al., "Low-Intensity Pulsed Ultrasound Stimulates Cell Proliferation and Proteoglycan Production in Rabbit Intervertebral Disc Cells Cultured in Alginate", *Biomaterials* 2006;27:354-361.

Juffermans et al., "Transient Permeabilization of Cell Membranes by Ultrasound-Exposed Microbubbles is Related to Formation of Hydrogen Peroxide", *Am. J. Physiol. Heart Circ. Physiol.* 2006;291:H1595-H1601.

Lee et al. "Low-Intensity Ultrasound Stimulation Enhances Chondrogenic Differentiation in Alginate Culture of Mesenchymal Stem Cells", *Artif. Organs*, 2006;30. Abstract Only.

Schumann et al., "Treatment of Human Mesenchymal Stem Cells with Pulsed Low Intensity Ultrasound Enhances the Chondrogenic Phenotype In Vitro", *Biorheology* 2006:43:431-443. Abstract Only.

van Wamel et al., "Vibrating Microbubbles Poking Individual Cells: Drug Transfer into Cells via Sonoporation", *Journal of Controlled Release* 2006;112:149-155.

An Informational Brochure entitled "EXOGEN Bone Healing System", provided by Orthopaedics, Smith & Nephew, Inc. 2006.

An Informational Brochure entitled "EXOGEN 4000+ Low-Intensity Ultrasound Fracture Healing System for the Treatment of Nonunion and Fresh Fractures", provided by Orthopaedics, Smith & Nephew, Inc. 2006.

An Informational Brochure entitled "Spinalogic Bone Growth Stimulator", provided by DonJoy, 2002.

* cited by examiner

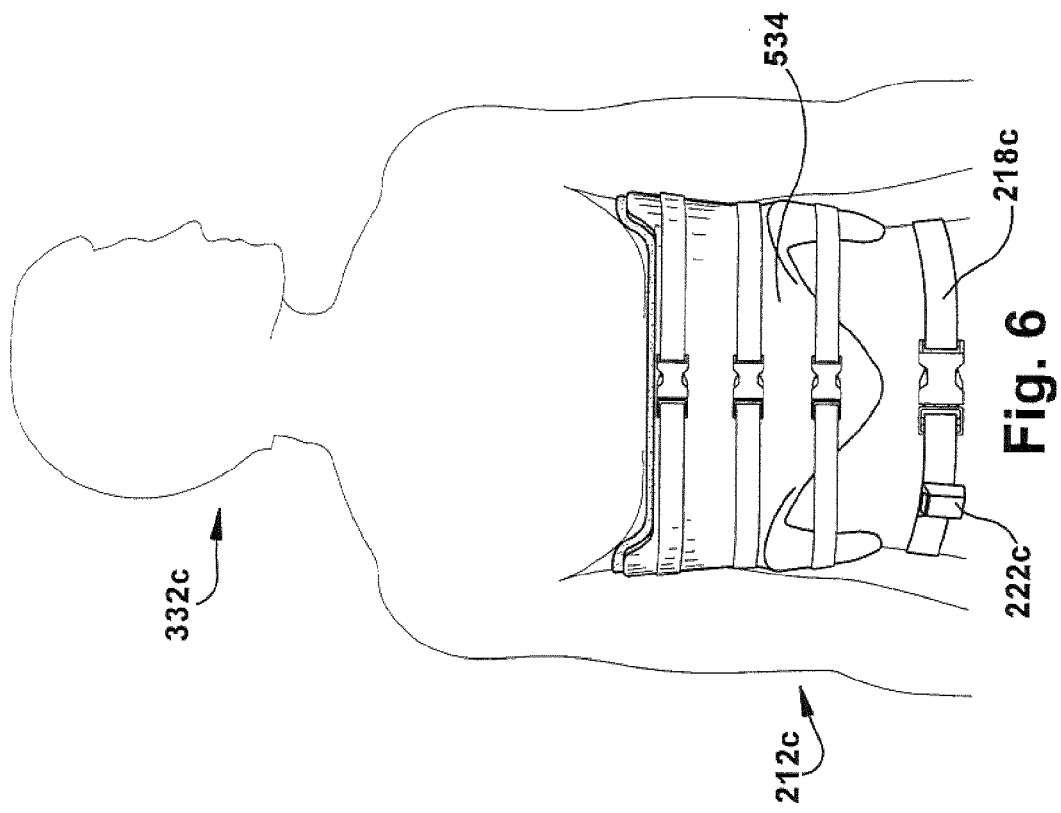
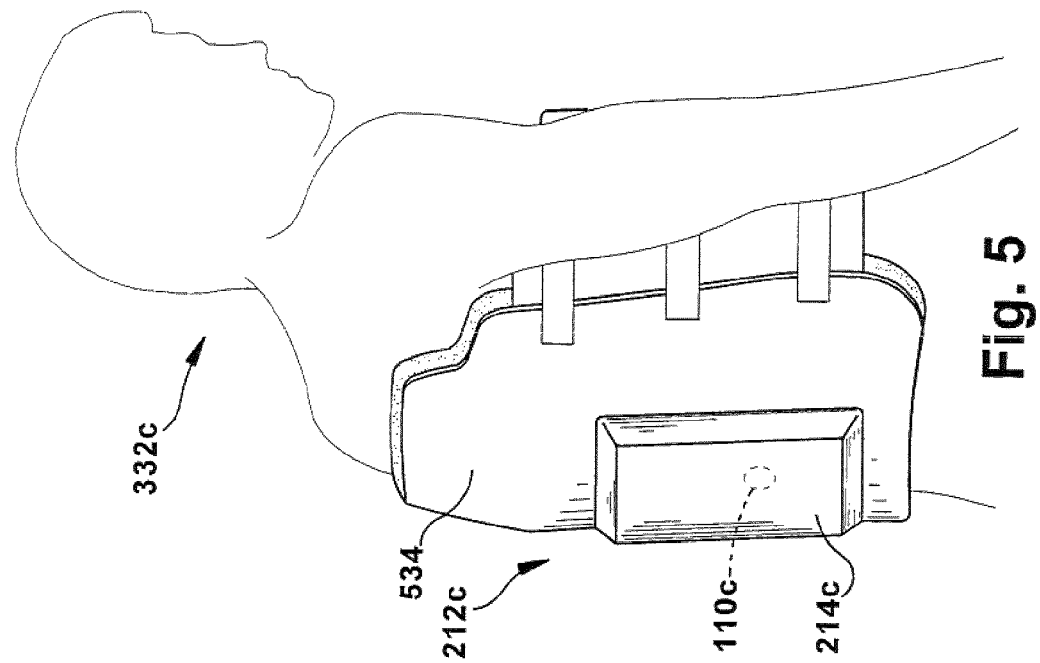

METHOD AND APPARATUS FOR REPAIR OF INTERVERTEBRAL DISCS

RELATED APPLICATION

This application claims priority from U.S. provisional patent application Ser. No. 60/905,210 filed on Mar. 6, 2007, the subject matter of which is incorporated herein by reference.

TECHNICAL FIELD

The present invention relates to a method and apparatus for repair of intervertebral discs and, more particularly, to an apparatus and method for using ultrasonic energy to repair degenerated intervertebral discs.

BACKGROUND OF THE INVENTION

FIG. 1 depicts a portion of the spinal structure of a patient. Two full vertebrae 100 are shown, with a third vertebra 102 cut away to show a cross-sectional view of an intervertebral disc 104. The intervertebral disc 104 includes an annulus fibrosus (concentric, interwoven collagenous fibers integrated with cartilage cells) 106 attached to the adjacent vertebrae 100, and a more central nucleus pulposus (a mass of degenerated collagen, proteoglycans, and water) 108 surrounded by the annulus fibrosus. Intervertebral disc 104 abnormalities have a high incidence in the population and may cause pain and discomfort if nerves are impinged upon or irritated. Disc abnormalities may be the result of trauma, repetitive use, metabolic disorders, and/or the aging process. Degenerative disc disease is generally used to refer to aging-related disc abnormalities, and this disease may include manifestations such as localized tears or fissures in the annulus fibrosus 106, localized disc herniations with contained or escaped extrusions, and chronic circumferential bulging discs.

Disc fissures occur rather easily after structural degeneration (a part of the aging process that may be accelerated by trauma) of fibrous components of the annulus fibrosus 106. Sneezing, bending, or just attrition can cause tears in these degenerated annulus fibers, thus creating a fissure. The fissure may be accompanied by extrusion of nucleus pulposus 108 material into or beyond the annulus fibrosus 106. The fissure itself may be the sole morphological change, above and beyond generalized degenerative changes in the connective tissue of the disc. Even if there is no visible extrusion, biochemicals within the disc may still irritate surrounding structures. Disc fissures can be debilitatingly painful. Initial treatment is symptomatic, including bed rest, pain killers and muscle relaxants. More recently, spinal fusion with cages has been performed when conservative treatment did not relieve the pain. The fissure may also be associated with a herniation of that portion of the annulus fibrosus 106.

With a contained disc herniation, there are no free nucleus pulposus 108 fragments in the spinal canal. Nevertheless, even a contained disc herniation is problematic because the outward protrusion can press on the spinal nerves or irritate other structures. In addition to nerve root compression, escaped nucleus pulposus 108 contents may chemically irritate neural structures. Current treatment methods include reduction of pressure on the annulus fibrosus 106 by removing some of the interior nucleus pulposus 108 material by percutaneous nuclectomy. However, complications include disc space infection, nerve root injury, hematoma formation, instability of the adjacent vertebrae 100, and collapse of the intervertebral disc 104 from decrease in height.

Another disc problem occurs when the intervertebral disc 104 bulges outward circumferentially in all directions and not just in one location. Over time, the disc weakens and takes on a "rolled" shape or circumferential bulge. Mechanical stiffness of the joint is reduced and the joint may become unstable. One vertebra 100 may settle on top of another. This problem continues as the body ages and contributes to shortened stature in old age. As the disc "roll" extends beyond the normal circumference, the disc height may be compromised, and foramina with nerve roots are compressed. In addition, osteophytes may form on the outer surface of the disc roll and further encroach on the spinal canal and foramina through which nerves pass. This condition is called lumbar spondylosis.

It has been thought that such circumferential bulging disc degeneration creates segmental instability which disturbs sensitive structures which in turn register pain. Traditional, conservative methods of treatment include bed rest, pain medication, physical therapy or steroid injection. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure may be carried out in conjunction with a discectomy. Other treatments include discectomy alone or disc decompression with or without fusion. Nuclectomy can be performed by removing some of the nucleus pulposus 108 to reduce pressure on the annulus fibrosus 106. However, potential complications from any of these treatments may include disc space infection, nerve root injury, hematoma formation, and instability of adjacent vertebrae 100.

These interventions have been problematic in that alleviation of back pain is unpredictable even if surgery appears to have been successful. In attempts to overcome these difficulties, new fixation devices have been introduced to the market, including, but not limited to, pedicle screws and interbody fusion cages. Although pedicle screws provide a high fusion success rate, there is still no direct correlation between fusion success and patient improvement in function and pain. Studies on fusion have demonstrated success rates of between 50% and 67% for pain improvement, and a significant number of patients have increased pain postoperatively. With the increasing life expectancy of the population, such degenerative disc disease and impairment of nerve function are becoming major public health problems. Therefore, methods of helping patients with degenerative disc problems, other than those just described, should be explored.

An example of an invasive application of energy for treating degenerative disc problems is disclosed in U.S. Pat. No. 5,433,739, issued Jul. 18, 1995 to Menno E. Sluijter et al. (hereafter referenced as "the '739 patent"). The '739 patent discloses placement of a radiofrequency (RF) electrode in an interior region of the intervertebral disc approximately at the center of the disc. RF power is applied, and heat then putatively spreads out globally throughout the disc. The '739 patent teaches the use of a rigid shaft which includes a sharpened distal end that penetrates through the annulus fibrosus and into the nucleus pulposus. In one embodiment, the shaft has to be rigid enough to permit the distal end of the RF electrode to pierce the annulus fibrosus, and the ability to maneuver its distal end within the nucleus pulposus is limited. In another embodiment, a somewhat more flexible shaft is disclosed. However, neither embodiment of the devices of the '739 patent permits access to the posterior, posterior lateral and posterior medial region of the disc, nor do they provide for focal delivery of therapy to a selected local region within the disc or precise temperature control at the annulus. The '739 patent teaches the relief of pain by globally heating the disc.

An example of a noninvasive application of energy for treating degenerative disc disease is disclosed in U.S. Pat. No. 6,254,553, issued Jul. 3, 2001 to Lars Lidgren et al. (hereafter referenced as "the '553 patent"). The '553 patent discloses an ultrasound transducer which can focus an ultrasonic field in an intervertebral disc, preferably in the nucleus pulposus, for heating the tissue therein. Portions of the intervertebral disc are heated to temperatures in the range of 45-80° C. so that the tissue in the focal area degenerates, thus reducing the pressure in the intervertebral disc and, in turn, reducing pressure against the spinal cord. To provide the ultrasonic energy, the patient is placed upon a treatment table and the ultrasonic transducers, along with monitoring and positioning equipment as desired, are suspended from a frame. The frame is movable with respect to the treatment table to compensate for patient positioning and movement, as the focal area must be precisely located, to avoid unintended heat damage to the patient's tissues.

SUMMARY OF THE INVENTION

In an embodiment of the present invention, a method of repairing an intervertebral disc of a patient's body is described. A target area of the intervertebral disc is identified. An ultrasound generator is placed proximate the target area and outside the patient's body. An area temperature at the target area is monitored. Ultrasonic energy is generated with the ultrasound generator within a predetermined energy range. The ultrasonic energy is adjusted in response to the area temperature exceeding a predetermined temperature range.

In an embodiment of the present invention, a method of treating degenerative disc disease of an intervertebral disc of a patient's body is described. A target area of the intervertebral disc is identified. The target area includes at least a portion of the intervertebral disc which has deteriorated due to degenerative disc disease. An ultrasound generator is placed proximate the target area and outside the patient's body. An area temperature at the target area is monitored. Ultrasonic energy is generated with the ultrasound generator within a predetermined energy range. At least one cell in the target area is regenerated using the ultrasonic energy. The ultrasonic energy is adjusted in response to the area temperature exceeding a predetermined temperature range.

In an embodiment of the present invention, an apparatus for repairing an intervertebral disc of a patient's body is described. An ultrasound generator provides ultrasonic energy to a target area of the intervertebral disc. The ultrasound generator is adapted for placement proximate the target area and outside the patient's body. The ultrasonic energy generated by the ultrasound generator is within a predetermined energy range. A temperature monitor senses an area temperature at the target area. A controller is adapted to control the generation of ultrasonic energy by the ultrasound generator. The controller adjusts the ultrasonic energy responsive to the area temperature exceeding a predetermined temperature range.

BRIEF DESCRIPTION OF THE DRAWINGS

For a better understanding of the invention, reference may be made to the accompanying drawings, in which:

FIG. 5 is a back view of a third embodiment of the present invention in a use position attached to a patient; and FIG. 6 is a front view of the embodiment of FIG. 5.

DESCRIPTION OF EMBODIMENTS

Figure 1:
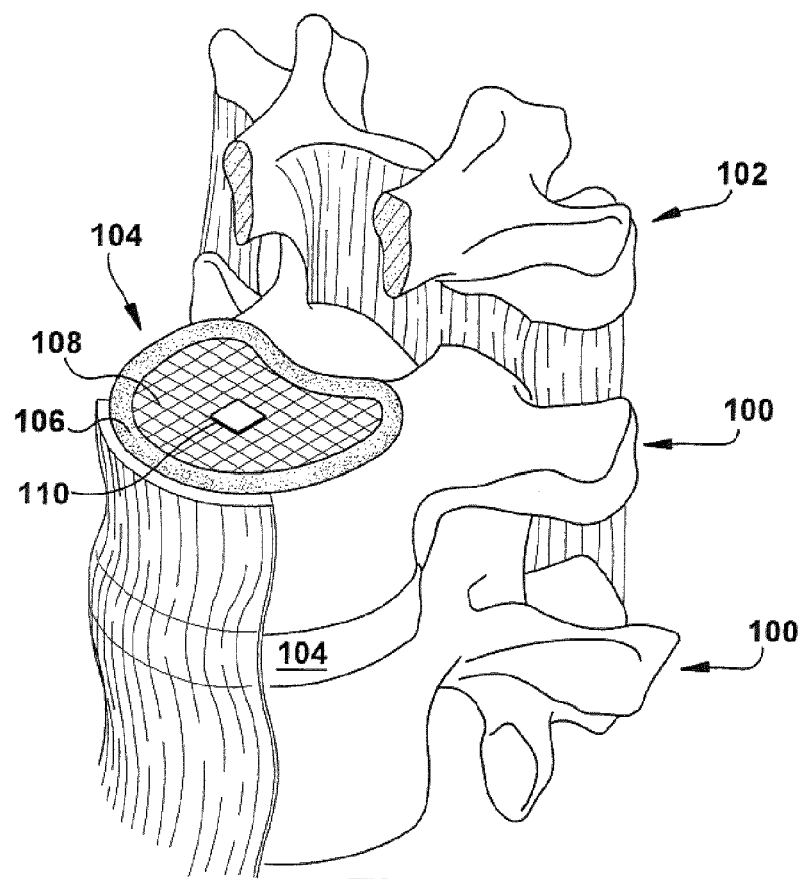
FIG. 1 is a partial perspective view of the environment of any embodiment of the present invention.

In accordance with the present invention, FIG. 1 depicts a target area 110 of an intervertebral disc 104 which includes cells (not shown) that have deteriorated, for example, as a result of degenerative disc disease. It is desirable to apply ultrasonic energy to the target area 110 to repair the deteriorated portion of the intervertebral disc 104 without causing a significant change in an area temperature (of the target area). For simplicity, the target area 110 is depicted as a selected group of adjacent squares within a grid superimposed upon the nucleus pulposus 108. However, the target area 110 may have any two-dimensional or three-dimensional shape, and may encompass any portion of the intervertebral disc 104, up to and including the entire intervertebral disc. Multiple target areas 110 may be treated ultrasonically, either concurrently or in succession.

The ultrasonic energy used to treat the target area 110 should be generated and controlled to avoid thermal effects on the cells in the target area. More specifically, it is known that ultrasound can be used to heat intervertebral disc 104 tissue and thereby ablate or deteriorate the cells therein. The present invention, in contrast, uses ultrasonic energy to repair a target area 110 of an intervertebral disc without allowing the area temperature to exceed a predetermined temperature range. For example, a top limit of the predetermined temperature range could be at or near the ambient body temperature of the patient. An example of a type of ultrasonic energy which may be used to produce the desired non-thermal repairing effect is pulsed low intensity ultrasonic energy with a pulse width of between about 10-20000 µs, e.g., 200 µs; a repetition rate of between about 100-1000 Hz, e.g., 1 KHz; an operation frequency of between about 0.5-2 MHz, e.g., 1.5 MHz; and temporal average intensities between about 200 mW/cm$^2$ to less than 30 mW/cm$^2$.

When ultrasonic energy having certain properties (such as the examples listed above) is provided to a target area 110 of an intervertebral disc 104, the ultrasound acts to repair one or more cells of the target area 110 and heal the intervertebral disc without producing significant thermal effects (e.g., ablation) on the cells. The healing mechanism may include at least partial regeneration of the cell. The healing mechanism may also or instead include enhanced matrix synthesis, and proteoglycans and collagen synthesis by nucleus pulposus and annulus fibrosus cells. Ultrasound has been shown to stimulate the maturation of tissue-engineered cartilage, and to enhance herniated disc reabsorption. Ultrasound can also stimulate chondrogenic differentiation of mesenchymal stem cells, increasing matrix production and collagen expression.

In order to avoid significant thermal effects, the area temperature must be monitored during application of the ultrasonic energy to the target area 110, and the ultrasonic energy must be adjusted responsive to the area temperature rising undesirably high. For example, generation of the ultrasonic energy could be ceased, or the focus of the ultrasonic energy could be shifted to a different target area (not shown), once the area temperature of the first target area 110 exceeds the predetermined temperature range. The ultrasonic energy could also or instead be temporarily redirected to a nontarget area (not shown) within the patient's body, optionally with a diffusion of focus, to allow the area temperature to return to the predetermined temperature range before treatment of the target area 110 is resumed. Additionally or alternatively, the intensity, duration, spacing, focus, or any other properties of the ultrasonic energy could be changed while the ultrasonic energy remains directed toward the target area 110, such that the area temperature is allowed to return to the predetermined temperature range during treatment of the target area.

Optionally, at least one pharmaceutical agent could be provided to the target area 110 at any time before, during, or after application of ultrasonic energy, and the ultrasonic energy acts to enhance at least one disc-healing quality of the pharmaceutical agent. Ultrasonic energy having the proper characteristics can increase membrane permeability, and aid in the absorption, diffusion and expression of various pharmaceutical agents. These agents may include anabolic growth factors such as BMPs, TGF-beta, IGF-1, PDGF, and FGF, among others. Inhibitors of catabolic enzymes and pro-inflammatory cytokines and free radicals could also be enhanced, e.g., MMP, collagenase, aggrecanase inhibitors, and/or NO, TNF, and IL-RA blockers. The stimulatory effects of ultrasonic energy on matrix synthesis may provide additive or synergistic benefit when combined with pharmaceutical and growth factor supplementation.

Similarly, at least one chondrocyte, which may be a patient's autologous chondrocyte, could be provided to the target area 110 at any time before, during, or after application of ultrasonic energy, and the ultrasonic energy acts to enhance at least one disc-healing quality of the chondrocyte. Ultrasonic energy can promote chondrogenesis of autologous disc cells and mesenchymal stem cells in a tissue-engineered scaffold. Ultrasonic energy can also enhance extracellular matrix, proteoglycans, and collagen synthesis.

FIGS. 2-6 depict differing embodiments of apparatus 212 for repairing an intervertebral disc of a patient's body. An ultrasound generator 214 may include one or more ultrasound transducers 216, each of which is operative to produce ultrasonic energy when excited. The generated ultrasonic energy produced by one or more ultrasound transducers 216 may be within a predetermined energy range, such as the previously discussed range. The ultrasound transducers 216 may be placed in any desired orientation relative to the patient and/or to each other, and one of ordinary skill in the art can readily design an ultrasound generator 214 having sufficient ultrasound transducers 216 to provide desired ultrasound generation properties. It should be understood that one or more ultrasound transducers 216 could be provided, assembled, housed, and/or controlled in any configuration or combination to generate ultrasonic energy, and a desired assembly or combination of ultrasound transducers 216 will hereafter be referenced as an ultrasound generator 214.

Figure 2:
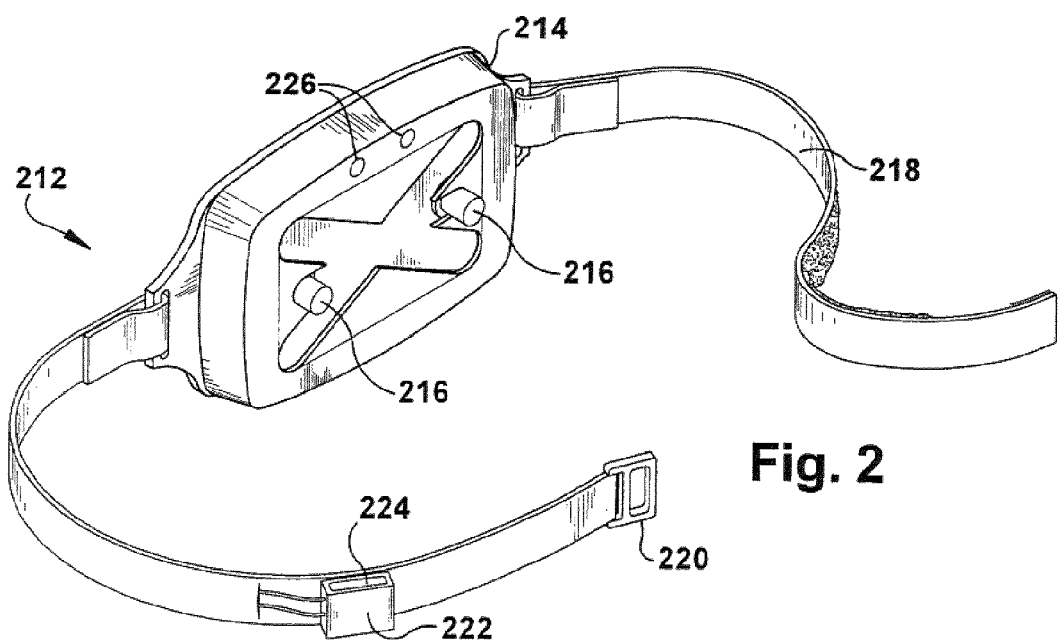
FIG. 2 is a perspective view of a first embodiment of the present invention.

In the first embodiment of FIG. 2, the ultrasound generator 214 is of a compact, unitary type and is carried by a harness, shown here as a belt 218. The belt 218 may be fashioned of any suitable material, in any suitable dimensions, but should be adapted for attachment to the patient's body. To such end, a fastener, such as the buckle 220, may be provided to facilitate a removable connection of the ultrasonic generator 214 to the patient. The belt 218, or any other type of harness used, should also be operative to maintain the portable ultrasound generator 214 in a desired position proximate the target area 110, which may be outside the patient's body, during generation of ultrasonic energy. Particularly when the ultrasound generator 214 is of the portable type, the apparatus 212 may be used by the patient in an independent manner, perhaps in a home situation. Thus, it is desirable to design and fashion the apparatus 212 to minimize the opportunities for user error to be introduced into the treatment process.

One way that user errors may be minimized is by the provision of a controller 222. The controller 222 is adapted to control the generation of ultrasonic energy by the ultrasound generator 214. Even when the ultrasound generator 214 is not portable and is used by a medical professional to treat the patient, a controller of some sort is necessary to control the generation of ultrasonic energy. However, when the ultrasound generator 214 is portable and adapted for home use, the controller 222 becomes even more important, due at least in part to the anticipated minimal training of the patient or other home user. Therefore, is contemplated that a basic treatment scheme may be preprogrammed into the controller 222, with a simple "start cycle" pushbutton 224 provided for one-touch control by the patient.

The controller 222 may be adapted to interface with a reader and/or programming device, to allow the supervising medical professional to set the initial treatment scheme, review the use history of the apparatus 212, and reprogram the apparatus with a different treatment scheme as desired. Optionally, the apparatus 212 may include a sensing device (not shown) to detect when the ultrasound generator 214 is not in sufficient ultrasonic contact with the target area 110. The controller 222 may be programmed to merely note such a lack-of-contact event, or may be equipped to produce an audible or visible signal (not shown) to help the user reposition the apparatus 212 as desired. It is also contemplated that a physical, chemical, or other type of marker could be provided on the patient's body, in addition to a sensing device (not shown) carried by the apparatus 212, to assist the user in positioning the apparatus properly in relation to the target area 110, perhaps through providing an audible or visible out-of-position signal (not shown) to the user.

Because the present invention seeks to avoid significant thermal effects on the cells of the target area 110, a temperature monitor 226 (two shown) may be provided to sense an area temperature of the target area in any desired manner. Though the temperature monitors 226 shown are carried by the ultrasound generator 214 on the apparatus 212, a temperature monitor (not shown) may also or instead be inserted into the patient's body. For example, a wired or wireless temperature monitor could be implanted into the patient's body for long-term use. As another example, a wired or wireless temperature monitor could be temporarily inserted into the patient's body in a probe-like manner as a short-term implant.

Figure 3:
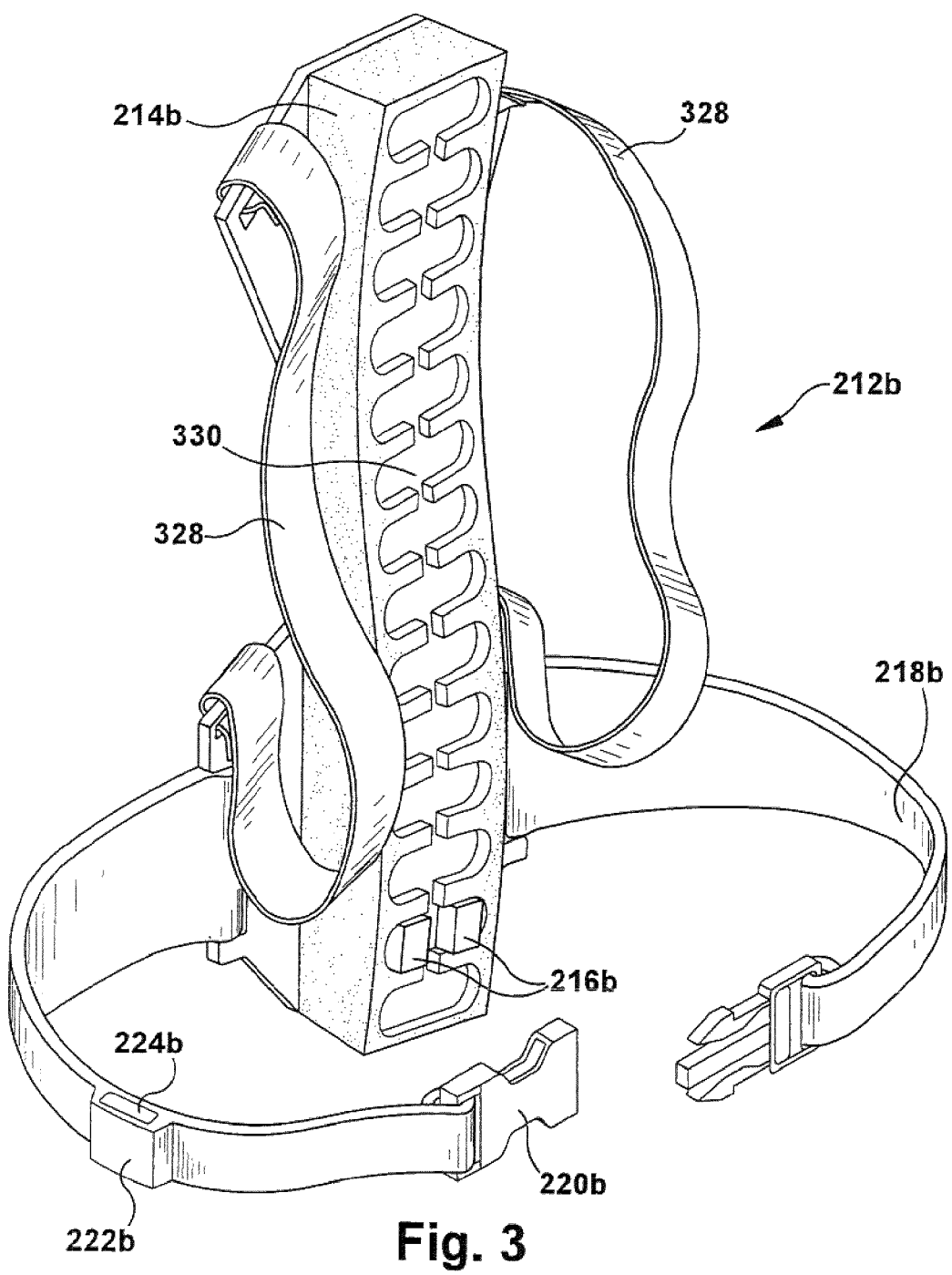
FIG. 3 is a perspective view of a second embodiment of the present invention.
Figure 4:
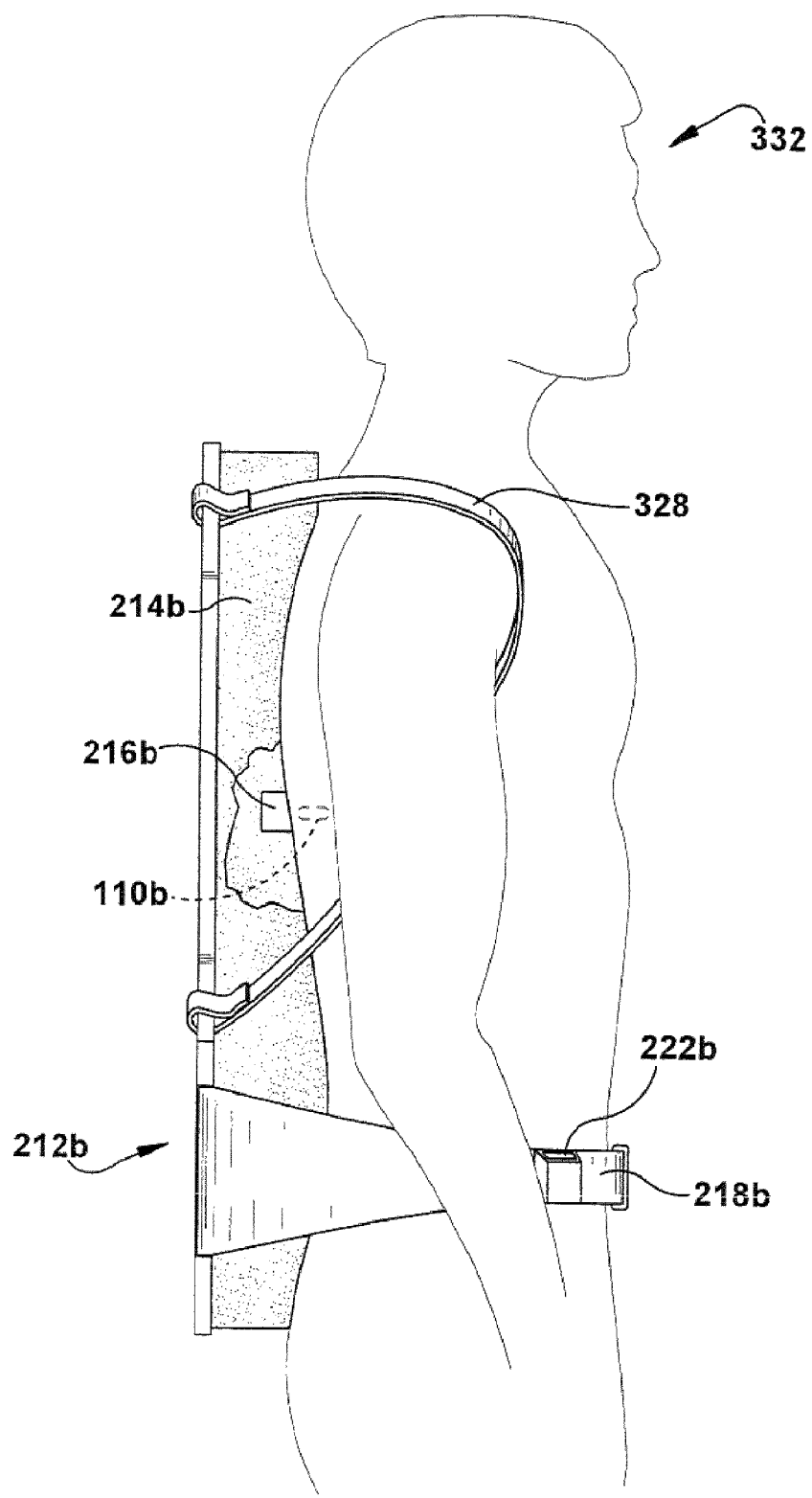
FIG. 4 is a side view of the embodiment of FIG. 3 in a use position attached to a patient.

FIGS. 3 and 4 depict a second embodiment of an apparatus 212b according to the present invention. The apparatus 212b of FIGS. 3 and 4 is similar to the apparatus 212 of FIG. 1 and therefore, structures of FIGS. 2 and 3 that are the same as or similar to those described with reference to FIG. 1 have the same reference numbers with the addition of a "b". Description of common elements and operation similar to those in the previously described embodiment will not be repeated with respect to the second embodiment.

Another feature of the apparatus 212b which may help minimize user errors is illustrated in FIGS. 3 and 4. When the apparatus 212b is in this second embodiment, the ultrasound generator 214b is of an elongate type and may be contoured to mimic the shape and curve of the patient's spine. In addition to the belt 218b, the harness of the second configuration includes a pair of shoulder straps 328, which may help with positioning and maintaining the ultrasound generator 214b in a desired orientation with respect to the target area 110b.

The ultrasound generator 214b of the second embodiment includes a positioning groove 330, which may be of any desired size, shape, orientation, and configuration. The positioning groove 330 is adapted to removably retain at least one ultrasound transducer 216b in a detent position adjacent a first chosen intervertebral disc (not shown). When ultrasonic energy is to be directed to a target area of a different chosen intervertebral disc (not shown), the ultrasound transducer 216b may be moved to another detent position within the positioning groove 330. Accordingly, the same ultrasound generator 214b can be used to provide ultrasonic energy, concurrently or serially, to target areas in several different, and perhaps spaced apart, intervertebral discs.

FIG. 4 depicts a patient 332 wearing the apparatus 212b. As can be readily seen, the contoured form of the ultrasound generator 214b echoes or mimics the natural curve of the patient's 332 back, to facilitate proper and repeatable placement of the ultrasound generator 214b proximate the target area 110b (shown in dashed line in FIG. 4). More specifically, at least one ultrasound transducer 216b is placed proximate the target area 110b and outside the patient's 332 body, as desired for provision of ultrasonic energy to the target area.

FIGS. 5 and 6 depict a third embodiment of an apparatus 212c according to the present invention. The apparatus 212c of FIGS. 5 and 6 is similar to the apparatus 212 of FIG. 1 and therefore, structures of FIGS. 5 and 6 that are the same as or similar to those described with reference to FIGS. 1-4 have the same reference numbers with the addition of a "c". Description of common elements and operation similar to those in the previously described embodiments will not be repeated with respect to the third embodiment.

FIGS. 5 and 6 depict a patient 332c wearing an apparatus 212c including a harness in the form of a corset 534. The corset 534 may help stabilize the trunk of the patient 332c and/or maintain the ultrasound generator 214c in a desired position proximate the target area 110c. The controller 222c may be attached to the corset 534 or, for the sake of accessibility by the patient 332c, may be carried separately on a belt 218, which may be attached to the corset 534 or separately provided.

Regardless of the embodiment of the apparatus 212, the operation of the present invention operates in the following manner. First, a target area 110 of an intervertebral disc 104 is identified. An ultrasound generator 214 is then placed proximate the target area 110, outside the body of a patient 332. Optionally, the ultrasound generator 214 may be attached to the body of the patient 332. For example, a belt 218, corset 534, or other harness could be provided when the ultrasound generator 214 is of a portable type.

Regardless of how it is placed into the desired position, the ultrasound generator 214 is used to generate ultrasonic energy within a predetermined energy range. An area temperature (of the target area 110) is monitored, and the ultrasonic energy being generated is adjusted in response to the area temperature exceeding a predetermined temperature range. Optionally, the ultrasonic energy could be discontinued—either by cessation or redirection—from being provided to the target area, in response to the area temperature exceeding a predetermined temperature range. At least one of a pharmaceutical agent, chondrocyte, autologous, or mesenchymal stem cell could be provided to supplement the disc-healing qualities of the ultrasonic energy.

Once a desired amount of ultrasonic energy has been provided to the target area 110, operation of the ultrasound generator 214 is concluded. If attached to the patient's body for treatment, the ultrasound generator 214 may be removed, and any suitable cleaning/storage tasks may be done to the apparatus 212, when reusable. The target area 110 may be inspected, such as with a noninvasive scanning device, at some time after the ultrasound treatment. Whether or not the target area 110 is inspected, ultrasonic energy may be repeatedly applied, on separate occasions, until a prescribed course of treatment is completed and/or the intervertebral disc 104 is sufficiently repaired.

While aspects of the present invention have been particularly shown and described with reference to the preferred embodiment above, it will be understood by those of ordinary skill in the art that various additional embodiments may be contemplated without departing from the spirit and scope of the present invention. For example, the ultrasound generator 214 need not be of the portable type. Any of the structures of the apparatus 212 may be made of any suitable material or combination of materials. The apparatus 212 may be used to treat a target area at any location in or on the body of the patient 332 and is not restricted to use in intervertebral disc or spinal applications. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A method of repairing an intervertebral disc of a patient's body, the method comprising the steps of:
   identifying a target area of the intervertebral disc;
   placing an ultrasound generator proximate the target area and outside the patient's body;
   monitoring an area temperature at the target area by inserting a temperature monitor into the target area of the patient's body;
   generating ultrasonic energy with the ultrasound generator within a predetermined energy range;
   regenerating at least one cell in the target area using the ultrasonic energy; and
   adjusting the ultrasonic energy in response to the area temperature exceeding a predetermined temperature range.

2. The method of claim 1, wherein the step of generating ultrasonic energy with the ultrasound generator within a predetermined energy range includes the step of generating pulsed low intensity ultrasonic energy with a pulse width of 10-20000 μs, repetition rate of 100-1000 Hz, operation frequency of 1.3-2 MHz, and temporal average intensities less than 100 mW/cm$^2$.

3. The method of claim 2, wherein the step of generating pulsed low intensity ultrasonic energy with a pulse width of 10-20000 μs, repetition rate of 100-1000 Hz, operation frequency of 1.3-2 MHz, and temporal average intensities less than 100 mW/cm$^2$ includes the step of generating pulsed low intensity ultrasonic energy with a pulse width of 200 μs, repetition rate of 1 KHz, operation frequency of 1.5 MHz, and temporal average intensities of 30 mW/cm$^2$.

4. The method of claim 1, wherein the step of adjusting the ultrasonic energy in response to the area temperature exceeding a predetermined temperature range includes the step of discontinuing the ultrasonic energy.

5. The method of claim 1, including the steps of:
   providing a pharmaceutical agent to the target area; and
   enhancing at least one disc-healing quality of the pharmaceutical agent with the ultrasonic energy.

6. The method of claim 1, including the steps of:

providing at least one chondrocyte to the target area; and
enhancing at least one disc-healing quality of the at least one chondrocyte with the ultrasonic energy.

7. The method of claim 1, wherein the step of placing an ultrasound generator proximate the target area and outside the patient's body includes the step of attaching a portable ultrasound generator to the patient's body.

8. A method of treating degenerative disc disease of an intervertebral disc of a patient's body, the method comprising the steps of:
identifying a target area of the intervertebral disc, the target area including at least a portion of the intervertebral disc which has deteriorated due to degenerative disc disease;
placing an ultrasound generator proximate the target area and outside the patient's body;
monitoring an area temperature at the target area by inserting a temperature monitor into the target area of the patient's body;
generating ultrasonic energy with the ultrasound generator within a predetermined energy range;
regenerating at least one cell in the target area using the ultrasonic energy; and
adjusting the ultrasonic energy in response to the area temperature exceeding a predetermined temperature range.

9. The method of claim 8, wherein the step of generating ultrasonic energy with the ultrasound generator within a predetermined energy range includes the step of generating pulsed low intensity ultrasonic energy with a pulse width of 200 µs, repetition rate of 1 KHz, operation frequency of 1.5 MHz, and temporal average intensities of 30 mW/cm$^2$.

10. The method of claim 8, including the steps of:
providing a pharmaceutical agent to the target area; and
enhancing at least one disc-healing quality of the pharmaceutical agent with the ultrasonic energy.

11. The method of claim 8, including the steps of:
providing at least one chondrocyte to the target area; and
enhancing at least one disc-healing quality of the at least one chondrocyte with the ultrasonic energy.

12. The method of claim 8, wherein the step of placing an ultrasound generator proximate the target area and outside the patient's body includes the step of attaching a portable ultrasound generator to the patient's body.

* * * * *